United States Patent
Koehler et al.

(10) Patent No.: US 7,596,203 B2
(45) Date of Patent: Sep. 29, 2009

(54) COMPUTER TOMOGRAPHY METHOD

(75) Inventors: Thomas Koehler, Norderstedt (DE); Andy Ziegler, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 39 days.

(21) Appl. No.: 11/575,716

(22) PCT Filed: Oct. 6, 2005

(86) PCT No.: PCT/IB2005/053286

§ 371 (c)(1),
(2), (4) Date: Mar. 21, 2007

(87) PCT Pub. No.: WO2006/040713

PCT Pub. Date: Apr. 20, 2006

(65) Prior Publication Data

US 2008/0095301 A1   Apr. 24, 2008

(30) Foreign Application Priority Data

Oct. 15, 2004   (EP)   ................................ 04105071

(51) Int. Cl.
*A61B 6/00*   (2006.01)
(52) U.S. Cl. ............................................................ 378/4
(58) Field of Classification Search ...................... 378/4
See application file for complete search history.

(56) References Cited

U.S. PATENT DOCUMENTS

| | | | |
|---|---|---|---|
| 4,272,820 A * | 6/1981 | Lux | 378/4 |
| 5,404,293 A | 4/1995 | Weng et al. | |
| 5,696,807 A * | 12/1997 | Hsieh | 378/109 |
| 5,744,802 A * | 4/1998 | Muehllehner et al. | 250/363.03 |
| 5,909,476 A | 6/1999 | Cheng et al. | |
| 5,909,477 A | 6/1999 | Crawford et al. | |
| 5,960,056 A | 9/1999 | Lai | |
| 6,400,789 B1 | 6/2002 | Dafni | |
| 6,480,561 B1 * | 11/2002 | Proksa | 378/16 |
| 6,490,337 B1 | 12/2002 | Nagaoka et al. | |
| 6,768,782 B1 * | 7/2004 | Hsieh et al. | 378/8 |
| 2003/0076927 A1 | 4/2003 | Nakashima et al. | |
| 2004/0081269 A1 * | 4/2004 | Pan et al. | 378/4 |
| 2004/0086074 A1 | 5/2004 | Taguchi | |
| 2004/0199065 A1 | 10/2004 | Braunstein | |
| 2004/0264626 A1 * | 12/2004 | Besson | 378/4 |
| 2005/0259780 A1 * | 11/2005 | Goodgame et al. | 378/4 |

OTHER PUBLICATIONS

"Iterative Reconstruction of Cone-Beam Data" http://dolphin.radiology.uiowa.edu/ge/Teaching/ct/node11.html Jun. 18, 2004.

* cited by examiner

*Primary Examiner*—Edward J Glick
*Assistant Examiner*—Alexander H Taningco

(57) ABSTRACT

The invention relates to a computer tomography method with a circular relative movement between the beam source and an iterative reconstruction method suitable therefor. The reconstruction method is substantially improved by deriving the first approximation image from a CT image, which is obtained from a prior acquisition during helical relative movement.

18 Claims, 2 Drawing Sheets

COMPUTER TOMOGRAPHY METHOD

Figure 1:
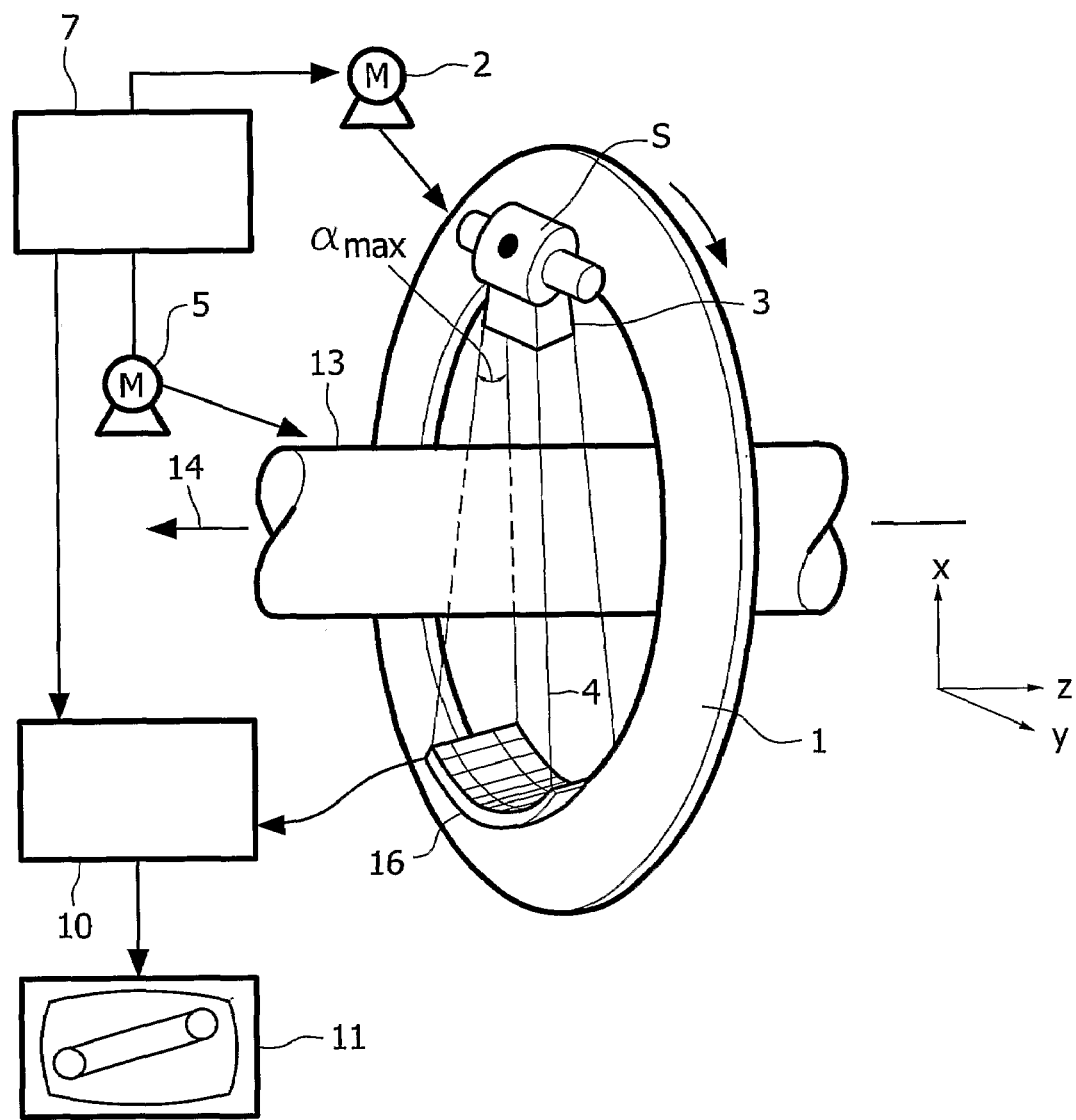

The invention relates to a computer tomography method, in which a beam source is used to generate a cone beam which passes through a scan region, or an object located in it, while a circular relative movement comprising a rotation about a rotation axis takes place between the beam source, on the one hand, and the scan region or object on the other hand. The invention also relates to a computer tomograph suitable for carrying out this computer tomography method, and to a computer program for controlling such a computer tomograph.

During the circular relative movement in this method, which is abbreviated to "circular cone beam CT" in the technical field, a two-dimensional or multi-line detector unit acquires measurement values which depend on the intensity in the beam on the other side of the scan region, i.e. on the attenuation of the radiation in the scan region. From these measurement values, it is possible to reconstruct the spatial distribution of the attenuation of the radiation in the three-dimensional scan region—hereafter abbreviated to "CT image", i.e. the object function. An exact reconstruction, however, is not possible—except in the plane of the circular relative movement—irrespective of whether the reconstruction is carried out by means of an analytical method, for example filtered back projection, or with the aid of an iterative method, to which the invention relates.

In such an iterative reconstruction method, the measurement values are compared with projection values computed from an approximation image used as an initial basis for the reconstruction. The comparison then gives a correction of the approximation image. The corrected approximation image is used as a basis for the next iteration cycle, by subsequently calculating projection values from it and comparing them with the measurement values, which leads to a further approximation image for another iteration cycle, etc. Since the contour of the object outside the plane of the circular relative movement is not known, all projection values of rays which travel at an angle to said plane are affected by errors which can lead to stronger or weaker artifacts in the CT image reconstructed in this way. These artifacts are commensurately more pronounced when the image details to be imaged are further away from the plane of the relative movement.

It is an object of the present invention to provide a method for iteratively reconstructing a CT image in a method of the type mentioned in the introduction, which leads to fewer artifacts i.e. an improved image quality.

This object is achieved according to the invention by a computer tomography method having the steps of:
a) using a beam source to generate a cone beam which passes through a scan region, or an object located in it, during a helical relative movement between the beam source, on the one hand, and the scan region or object on the other hand, comprising a rotation about a rotation axis and a displacement parallel to the rotation axis,
b) using a detector unit to acquire a first set of measurement values during the relative movement, which depend on the intensity in the beam on the other side of the scan region,
c) reconstructing a first CT image from the first set of measurement values,
d) using a beam source to generate a cone beam which passes through a scan region, or an object located in it, in conjunction with a circular relative movement between the beam source and the scan region or object, at a position of the scan region which the beam has already crossed during the helical relative movement,
e) using a detector unit to acquire a second set of measurement values during the circular relative movement,
f) iteratively reconstructing a second CT image from the second set of measurement values, an approximation image in each iteration cycle being corrected by comparing projection values calculated from the approximation image with the measurement values, and the first approximation the image being derived from the first CT image.

In the invention therefore, a set of measurement values is acquired not only during the circular relative movement but also during a prior helical relative movement, which comprises a rotation about the rotation axis and a displacement in the direction of the rotation axis. From the set of measurement values acquired during the helical relative movement, it is possible to reconstruct a first CT image from which a first approximation image is derived for the iterative reconstruction method. This gives a substantially better image quality of the iteratively reconstructed image, even if the first CT image used as a basis is strongly affected by noise.

At this point, it should be mentioned that it is already known from U.S. Pat. No. 6,480,561 to acquire a first set of measurement values in conjunction with a helical relative movement before a CT scan. The (three-dimensional) CT image derived therefrom is used to calculate a (two-dimensional) projection image which corresponds to a so-called "pilot scan" that conventionally precedes a CT scan, during which the beam source and the object are displaced relative to each other in the direction of the rotation axis—without any rotation—and which can be used to establish the scan region for the actual CT scan.

The embodiment as claimed in claim 2 has the advantage that the prior acquisition during the helical relative movement entails only a comparatively small increase of the dose in the scan region, which is important especially in medical applications. For example, the dosage during the helical relative movement is at least ten times, preferably from one hundred to one thousand times, less than the dosage during the circular relative movement.

The embodiment as claimed in claim 3 reduces the noise in the first approximation image (which is encountered particularly when the first set of measurement values was acquired with a very low dosage), which leads to a further improvement of the image quality.

The embodiment as claimed in claim 4 is important especially for CT scans of the heart, because in this case a large proportion of the measurement values which are acquired during a circuit cannot be used for the reconstruction because the acquisition took place during a phase in which the heart movement was relatively strong.

Claim 5 describes a computer tomograph for carrying out the method according to the invention, and claim 6 describes a computer program for controlling a computer tomograph as claimed in claim 5.

These and other aspects of the invention are apparent from and will be elucidated with reference to the embodiments described hereinafter.

Figure 2:
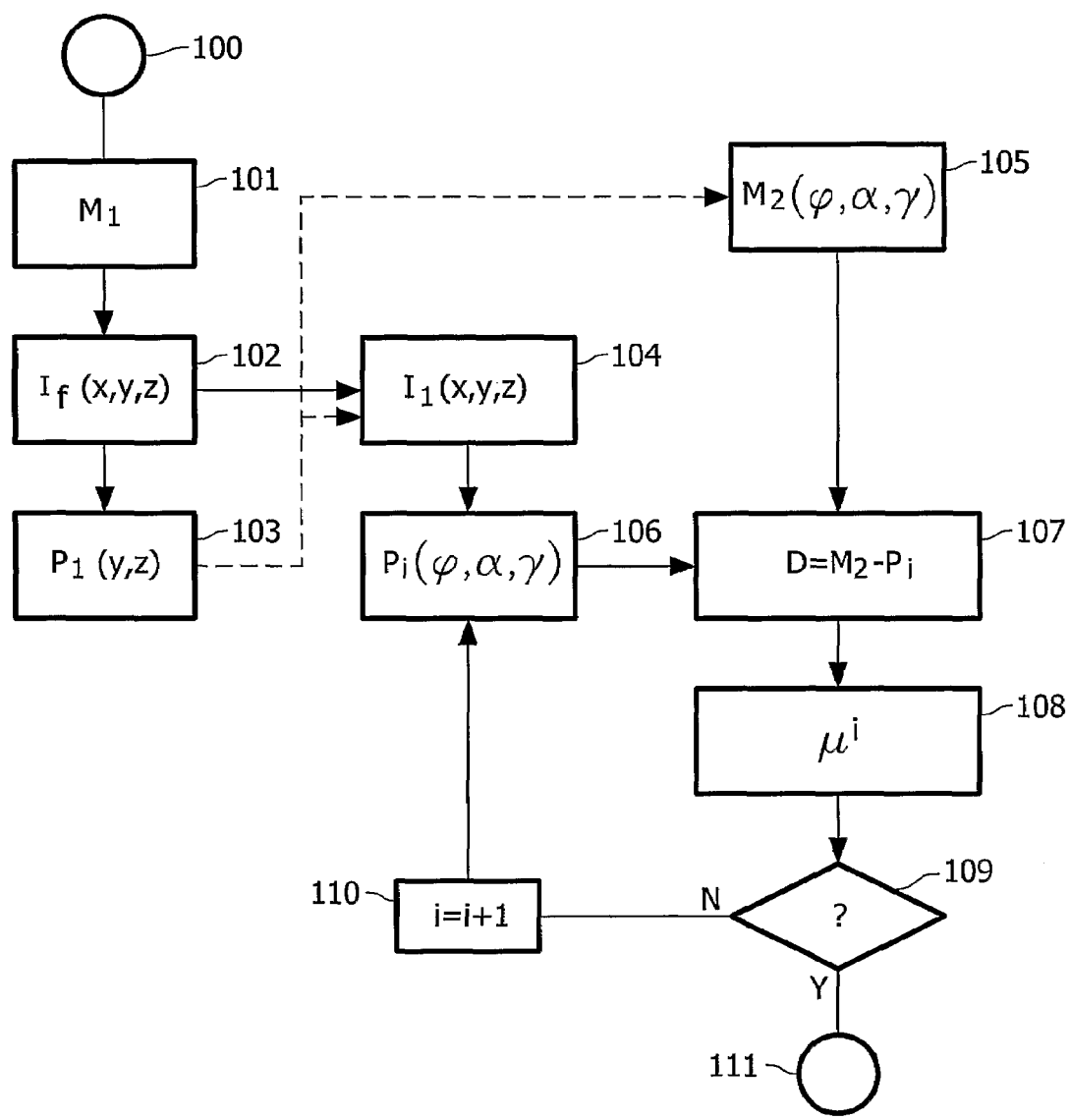
Figure 3:
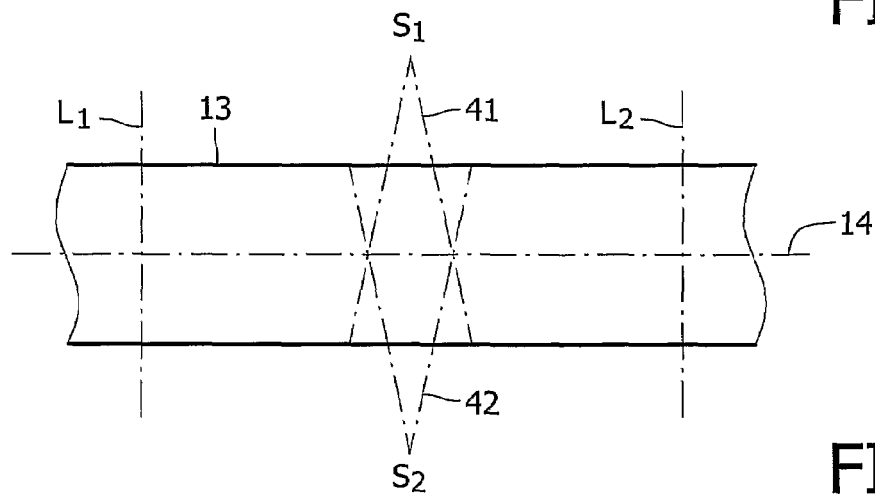

In the drawings:

FIG. 1 shows a computer tomograph with which the method according to the invention can be carried out, FIG. 2 shows a flow chart of the method according to the invention, and FIG. 3 shows the parts of the scan region irradiated during the circular relative movement.

The computer tomograph represented in FIG. 1 comprises a gantry 1, which can rotate about a rotation axis 14 extending parallel to the z direction of the x,y,z coordinate system represented in FIG. 1. To this end, the gantry 1 is driven by a motor 2 with a preferably constant but adjustable angular speed. A beam source S, for example an X-ray emitter, is fastened on the gantry. It is provided with a collimator arrangement 3 which extracts a cone beam 4, i.e. a beam which has a non-zero finite extent both in the z direction and in a direction perpendicular thereto (i.e. in a plane perpendicular to the rotation axis), from the radiation generated by the beam source S.

The beam 4 passes through a scan region 13 in which there may be an object, for example a patient on a patient support table (neither represented in detail). The scan region 13 has the shape of the cylinder. After passing through the scan region 13, the X-ray beam 4 strikes a two-dimensional detector unit 16 which is fastened on the gantry 1 and comprises a number of detector rows, respectively having a multiplicity of detector elements. The detector rows lie in a plane perpendicular to the rotation axis, preferably on an arc of a circle around the beam source S; they may nevertheless be shaped differently, for example describing an arc of a circle around the rotation axis 14 or in a straight line. Each detector element which is struck by the beam 4 delivers a measurement value for a ray of the beam 4 in each position of the beam source.

The aperture angle of the beam 4 denoted by $\alpha_{max}$ (the aperture angle is defined as the angle which a ray, lying at the edge of the beam 4 in a plane perpendicular to the rotation axis 14, makes with a plane defined by the beam source S and the rotation axis 14) in this case determines the diameter of the object cylinder within which the object to be scanned is located during acquisition of the measurement values. The scan region 13—or the object or patient support table—can be moved parallel to the rotation axis 14, i.e. the z axis, by means of a motor 5. Equivalently, however, the gantry may also be moved in this direction.

If the motors 5 and 2 are operating simultaneously, the beam source S and the detector unit 16 describe a helical trajectory relative to the scan region 13. If the motor 5 for the advance in the z direction is stationary and the motor 2 makes the gantry rotate, however, then a circular trajectory or relative movement is obtained for the beam source S and the detector unit 16 relative to the scan region 13.

The measurement values acquired by the detector unit 16 are delivered to an image processing computer 10 which reconstructs a CT image therefrom, i.e. the absorption distribution in a part of the scan region 13, and for example displays it on a monitor 11. The two motors 2 and 5, the image processing computer 10, the beam source S and the transfer of measurement values from the detector unit 16 to the image processing computer 10 are controlled by a control unit 7.

FIG. 2 illustrates the procedure of a measurement and reconstruction method which can be carried out with the computer tomograph according to FIG. 1.

After the initialization in block 100, the motors 2 and 5 and the beam source S are switched on. The driving by the two motors 2 and 5 leads to a helical movement of the beam source relative to the rotation axis 14, the beam 4 emitted by the beam source passing through the scan region 13 and being detected by the detector unit 16. The dosage is in this case between 1 per mile and 1 percent of the dosage generated during the subsequent circular relative movement, so that the radiation exposure during the helical relative movement is comparatively small for medical scans.

A first set of measurement values $M_1$, which correspond to the line integral of the attenuation of the radiation in the scan region along rays from the beam source to the individual detector elements, is then derived from the detector signals.

A first CT image $I_f(x,y,z)$, which represents the spatial distribution of the attenuation in the scan region, is reconstructed from the first set of measurement values in step 102. Since the voxels in the scan region are irradiated from an angular range of at least 180° during a helical relative movement, the first and last ray of each voxel coming from opposite directions, an exact reconstruction is in principle possible here. Because of the low signal/noise ratio due to the low dosage, however, only a limited image quality is obtained.

An image $P_1(x,y,z)$ which represents a projection of the first CT image, for example onto the yz plane, is derived from the first CT image $I_f(x,y,z)$ in step 103. With the aid of the projection image it is then possible to establish—by a user or automatically according to predetermined criteria—which region should be irradiated with a circular relative movement during the subsequent CT scan. This is represented in FIG. 3, where the planes perpendicular to the rotation axis 14 which are indicated by the lines L1 and L2 represent the limits within which the scan region 13 is imaged by the first CT image $I_f(x,y,z)$. This selection is symbolized in FIG. 2 by a dashed line from block 103 to blocks 104 and 105, which have yet to be explained.

After having established which part of the region imaged by the first CT image is intended to be imaged by the subsequent circular relative movement of the beam source, an image $I_1(x,y,z)$ comprising all the voxels which radiation will strike during the subsequent circular relative movement is derived from the first CT image $I_f$ in step 104. This is an axisymmetric region relative to the rotation axis, which is symbolized in FIG. 3 by the two beams 41, 42 emitted from the beam source positions $S_1$ and $S_2$. If it has not already taken place during the reconstruction of the first CT image in step 102, lowpass filtering or smoothing must be carried out in step 104 so that the further image processing is not disturbed by the noise contained in the first CT image.

Only the motor 2 is switched on in step 105, while the motor 5 is stationary so that the beam source describes a circular path relative to the rotation axis at the position established in step 103. The beam source S is switched on at the same time, the dosage in the beam 4 being substantially higher than during the prior helical scanning. The detector signals then received by the detector elements of the detector 16 are logarithmed so that a second set of measurement values $M_2(\phi,\alpha,\gamma)$ is acquired, each of which corresponds to the line integral of the attenuation along a ray from the beam source to a detector element. These measurement values depend on the position $\phi$ of the beam source relative to the rotation axis 14, on the fan angle $\alpha$ (which is the angle made between the ray associated with the measurement value and the perpendicular to the rotation axis 14) and on the cone angle $\gamma$ (which is the angle made between the ray in a plane containing the rotation axis and a perpendicular to the rotation axis).

After the second set of measurement values has thereby been acquired in step 105, an iterative reconstruction method comprising a number of iteration cycles with the processing steps represented in blocks 106 to 110 is carried out in order to reconstruct a second CT image.

Projection values $P_i(\phi,\alpha,\gamma)$ based on an approximation image are calculated in step 106 for rays which coincide in terms of position and direction with the rays for which the measurement values $M_2(\phi,\alpha,\gamma)$ were acquired in step 105. The first approximation image in this iteration method is the image $I_1(x,y,z)$ generated in step 104. If this approximation image exactly reproduced the attenuation distribution in the scan region and if the measurement values $M_2(\phi,\alpha,\gamma)$ were not affected by errors, then each projection value (obtained by summing the attenuation values of those voxels in the approximation image through which the same ray passes) should match the measurement value which was measured along the same ray. This condition is not satisfied in practice, however, so that discrepancies occur.

For a ray, therefore, the difference of the measurement value $M_2(\phi,\alpha,\gamma)$ and the projection value $P_i(\phi,\alpha,\gamma)$ which belongs to the same ray is formed in step 107—according to the relation $$D=M_2(\phi,\alpha,\gamma)-P_i(\phi,\alpha,\gamma) \quad (1)$$

This is repeated for all the rays which were calculated in the same position $\phi$ of the beam source. The approximation image can then be corrected using the differences formed in this way.

To this end, in step 108, the attenuation values are recalculated for each voxel j on a ray according to the relation $$\mu^i(j)=\mu^{i-1}(j)+\lambda \cdot d \cdot s_j \quad (2)$$

where $\mu(j)^{i-1}$ and $\mu(j)^i$ are the previous and new attenuation values for the voxel j, $\lambda(<1)$ is a parameter controlling the convergence of the method, $s_j$ is the length of the ray inside the voxel j and d corresponds to the ratio of the difference D and the sum of the squares of the lengths $(s_j)$ of the ray inside the individual voxels on the ray. This is repeated for all the rays which were acquired in the same position $\phi$ of the beam source, so that the attenuation values of all of the voxels have been recalculated at the end of step 108.

A check is made in step 109 as to whether a particular criterion is satisfied. This criterion may be a sufficient match between the projection values and the measurement values, or the execution of a particular number of iteration cycles, i.e. a particular duration of the iteration method. The termination criterion may, however, also be satisfied if a user terminates the iteration, for example because the image quality is sufficient.

If the termination criterion has not yet been satisfied, then the count index i is increased by 1 in step 110 (block 110) and new projections $P_i(\phi,\alpha,\gamma)$ are then calculated in block 106—but this time based on the attenuation values $\mu^i$ recalculated in step 108. This is followed in step 107 by a new comparison of the projection values with the measurement values—but for a different position $\phi$ of the beam source than in the previous iteration cycle, and the attenuation values are recalculated as a function of the difference in step 108.

If a termination criterion is reached in step 109, the method is ended 111. The last approximation image compiled in block 108 then represents the second CT image, which can be visualized in a suitable way. The image quality is significantly improved compared with analytical reconstruction methods or other iterative reconstruction methods.

The iteration method described above is known in the technical field as the ART method (ART=algebraic reconstruction technique). Instead of this iteration method, another iteration method may also be employed in order to reconstruct the second CT image, for example the method known as the "maximum likelihood—expectation maximization" (ML-EM) method in the technical field. In this method, it is merely necessary to modify steps 107 and 108. Instead of the differences of the measurement values and the projection values in step 107, the ratio of these values should be formed and the attenuation values should be corrected as a function of these ratios in step 108.

In step 105, the measurement values $M_2(\phi,\alpha,\gamma)$ may be acquired for a plurality of circuits of the beam source on the circular path. CT scans of the heart are one application of such acquisition, in which case only the measurement values acquired in a resting phase of the heart between two heart actions can be employed for the reconstruction. The circuit times of the beam source, for example 0.4 second, are not short enough to acquire enough measurement values in the resting phase of the heart. In this case, measurement values should also be acquired in subsequent circuits and in the resting phases of the subsequent heart actions, so as to obtain a full set of measurement values.

Another possible application of measurement values acquired in a plurality of circuits is the continuous representation of a slowly changing object (CT fluoroscopy). A set of measurement values is reconstructed in each circuit, from which it is respectively possible to reconstruct a CT image that represents the object in a particular motion phase. The image derived from the first CT image is used as a first approximation image in the iterative reconstruction process for all these CT images.

In the exemplary embodiment represented in FIG. 1, the beam source rotates about the rotation axis with a circular relative movement. In order to scan objects, it is nevertheless possible to leave the beam source immobile and to make the object rotate about the rotation axis. The invention can also be employed in an electron beam computer tomograph in which the radiation is generated on a ring enclosing the scan region, which is struck by an electronically deflected electron beam. In this case, the focus at which the electron beam strikes the ring should be regarded as a beam source in the context of the invention.

The invention claimed is:

1. A computer tomography method comprising:
   generating a first cone beam using a beam source which passes through a scan region, or an object located in the scan region, during a helical relative movement between the beam source, and the scan region or object, comprising a rotation about a rotation axis and a displacement parallel to the rotation axis;
   acquiring a first set of measurement values using a detector unit during the relative movement, which depend on the intensity in the first cone beam on another side of the scan region;
   reconstructing a first CT image from the first set of measurement values;
   generating a second cone beam using the beam source which passes through the scan region, or the object, in conjunction with a circular relative movement between the beam source and the scan region or object, at a position of the scan region which the first cone beam has already crossed during the helical relative movement;
   acquiring a second set of measurement values using the detector unit during the circular relative movement; and
   iteratively reconstructing a second CT image from the second set of measurement values by correcting an approximation image derived from the first CT image in each iteration cycle by comparing projection values calculated from the approximation image with the second set of measurement values.

2. A computer tomography method as claimed in claim 1, wherein a radiation dosage in the first cone beam emitted by the beam source during the helical relative movement is substantially less than a radiation dosage in the second cone beam emitted by the beam source during the circular relative movement.

3. A computer tomography method as claimed in claim 1, wherein a spatial resolution of the approximation image is reduced by lowpass filtering or a smoothing method.

4. A computer tomography method as claimed in claim 1, wherein the circular relative movement comprises a plurality of circuits.

5. The computer tomography method as claimed in claim 1, further comprising using a projection of the first CT image to establish the position of the scan region through which the second cone beam passes during the circular relative movement between the beam source and the scan region or object.

6. The computer tomography method as claimed in claim 5, wherein the position of the scan region is established according to predetermined criteria.

7. A computer tomograph, comprising:
   a beam source for generating a first cone beam which passes through a scan region, or an object located in the scan region;
   a detector unit coupled to the beam source;
   a drive arrangement for making the beam source rotate relative to the object contained in the scan region about a rotation axis and/or for making the beam source move relative to the object parallel to the rotation axis;
   a reconstruction unit for reconstructing a spatial distribution of the absorption inside the scan region from the measurement values acquired by the detector unit, and
   a control unit for controlling the beam source, the detector unit, the drive arrangement and the reconstruction unit according to the following steps:
      generating the first cone beam source which passes through the scan region, or an object located in the scan region, during a helical relative movement between the beam source, and the scan region or object on the other hand, comprising a rotation about the rotation axis and a displacement parallel to the rotation axis;
      acquiring a first set of measurement values using a detector unit during the relative movement, which depends on an intensity of radiation in the first cone beam on another side of the scan region;
      reconstructing a first CT image from the first set of measurement values;
      generating a second cone beam using the beam source which passes through the scan region, or the object, in conjunction with a circular relative movement between the beam source and the scan region or object, at a position of the scan region which the first cone beam has already crossed during the helical relative movement;
      acquiring a second set of measurement values using the detector unit during the circular relative movement; and
      iteratively reconstructing a second CT image from the second set of measurement values by correcting an approximation image derived from the first CT image in each iteration cycle by comparing projection values calculated from the approximation image with the second set of measurement values.

8. The computer tomograph as claimed in claim 7, wherein a radiation dosage in the first cone beam emitted by the beam source during the helical relative movement is substantially less than a radiation dosage of the second cone beam emitted by the beam source during the circular relative movement.

9. The computer tomograph as claimed in claim 7, wherein a spatial resolution of the approximation image is reduced by lowpass filtering or a smoothing method.

10. The computer tomograph as claimed in claim 7, wherein the circular relative movement comprises a plurality of circuits.

11. The computer tomograph as claimed in claim 7, further comprising using a projection of the first CT image to establish the position of the scan region through which the second cone beam passes during the circular relative movement between the beam source and the scan region or object.

12. The computer tomograph as claimed in claim 11, wherein the position of the scan region is established according to predetermined criteria.

13. A computer with computer readable medium storing instructions that when executed on the computer, cause a control unit of a computer tomography to control a beam source, a detector unit of a drive arrangement and a reconstruction unit, according to the following procedure:
   generating a first cone beam using the beam source which passes through a scan region, or an object located in it, during a helical relative movement between the beam source, and the scan region or object, comprising a rotation about a rotation axis and a displacement parallel to the rotation axis;
   acquiring a first set of measurement values using a detector unit during the relative movement, which depends on an intensity of radiation in the first cone beam on another side of the scan region;
   reconstructing a first CT image from the first set of measurement values;
   generating a second cone beam using the beam source which passes through the scan region, or the object, in conjunction with a circular relative movement between the beam source and the scan region or object, at a position of the scan region which the first cone beam has already crossed during the helical relative movement;
   acquiring a second set of measurement values using the detector unit during the circular relative movement; and
   iteratively reconstructing a second CT image from the second set of measurement values by correcting an approximation image derived from the first CT image in each iteration cycle by comparing projection values calculated from the approximation image with the second set of measurement values.

14. The computer as claimed in claim 13, wherein a radiation dosage in the first cone beam emitted by the beam source during the helical relative movement is substantially less than a radiation dosage in the second cone beam emitted by the beam source during the circular relative movement.

15. The computer as claimed in claim 13, wherein a spatial resolution of the approximation image is reduced by lowpass filtering or a smoothing method.

16. The computer as claimed in claim 13, wherein the circular relative movement comprises a plurality of circuits.

17. The computer as claimed in claim 13, further comprising using a projection of the first CT image to establish the position of the scan region through which the second cone beam passes during the circular relative movement between the beam source and the scan region or object.

18. The computer as claimed in claim 17, wherein the position of the scan region is established according to predetermined criteria.

* * * * *